United States Patent [19]
Klitzman et al.

[11] Patent Number: 6,013,122
[45] Date of Patent: Jan. 11, 2000

[54] TATTOO INKS

[75] Inventors: Bruce Klitzman, Durham, N.C.; Kim Edward Koger, Tequesta, Fla.

[73] Assignee: Option Technologies, Inc., Durham, N.C.

[21] Appl. No.: 09/135,814

[22] Filed: Aug. 18, 1998

[51] Int. Cl.[7] .................................................. C09D 11/00
[52] U.S. Cl. .................................. 106/31.03; 106/31.15; 106/31.32; 106/31.33; 106/31.64; 106/31.65
[58] Field of Search ............................ 106/31.03, 31.15, 106/31.32, 31.33, 31.64, 31.65

[56] References Cited

U.S. PATENT DOCUMENTS

| | | | |
|---|---|---|---|
| 2,487,557 | 11/1949 | Jourgensen | 106/31.03 |
| 2,735,780 | 2/1956 | Le Compte et al. | 106/31.03 |
| 3,011,899 | 12/1961 | Bergman | 106/31.03 |
| 3,272,585 | 9/1966 | Rafferty et al. | 106/31.03 |
| 3,640,889 | 2/1972 | Stewart | 106/31.03 |
| 3,708,334 | 1/1973 | Firth et al. | 106/31.03 |
| 3,873,687 | 3/1975 | Demko | 106/31.03 |
| 4,155,886 | 5/1979 | DeGoler | 106/31.03 |
| 4,214,490 | 7/1980 | Chizek | 81/9.22 |
| 4,280,813 | 7/1981 | DeGoler | 106/31.03 |
| 4,610,806 | 9/1986 | Rosen | 106/31.03 |
| 4,861,627 | 8/1989 | Mathiowitz et al. | 427/213.31 |
| 4,897,268 | 1/1990 | Tice et al. | 424/422 |
| 4,898,734 | 2/1990 | Mathiowitz et al. | 424/426 |
| 4,900,556 | 2/1990 | Wheatley et al. | 424/450 |
| 4,921,757 | 5/1990 | Wheatley et al. | 428/402.2 |
| 4,933,185 | 6/1990 | Wheatley et al. | 424/461 |
| 5,041,292 | 8/1991 | Feijen | 424/484 |
| 5,087,461 | 2/1992 | Levine et al. | 426/96 |
| 5,384,333 | 1/1995 | Davis | 514/772.3 |
| 5,601,859 | 2/1997 | Penaluna | 426/5 |

FOREIGN PATENT DOCUMENTS

| | | | |
|---|---|---|---|
| 2705615 | 12/1994 | France . | |
| 34 20 867 | 12/1985 | Germany . | |
| 137175 | 10/1980 | Japan | 106/31.03 |
| 98202 | 4/1993 | Japan | 106/31.03 |

*Primary Examiner*—Helene Klemanski
*Attorney, Agent, or Firm*—Browdy and Neimark

[57] ABSTRACT

Tattoo inks are composed of pigments or dyes combined with a tattoo pigment vehicle which entraps, encases, incorporates, complexes, encapsulates, or is otherwise associated with the pigment to form pigment/vehicle complexes that retain the pigment in the tissue. The vehicle can be chosen so that pigments which alone are unsuitable for tattooing can be used for tattooing and optionally can be retained in the tissue permanently. Alternatively, the vehicle renders the tattoo erasable, wherein the tattoo disappears after imposition of an exogenous energy. Alternatively, the tattoo pigment vehicle renders the tattoo semi-permanent, so that the tattoo spontaneously disappears at a predetermined time.

16 Claims, 2 Drawing Sheets

TATTOO INKS

FIELD OF THE INVENTION

The present invention relates to the combination of pigments and vehicles (i.e., coloring materials) for preparing tattooing inks.

BACKGROUND OF THE INVENTION

Humans have been applying tattoos to the skin for over 8000 years. The inks and dyes used were historically derived from substances found in nature and comprise a heterogeneous suspension of pigmented particles and other impurities. A well-known example is India ink, a suspension of carbon particles in a liquid.

Tattoos are produced by applying tattoo ink into the dermis, where the ink remains permanently. This technique introduces the pigment suspension through the skin by an alternating pressure-suction action caused by the elasticity of the skin in combination with the up-and-down movement of the needles. Water and other carriers for the pigment introduced into the skin diffuse through the tissues and are absorbed. The insoluble pigment particles are deposited in the dermis where initially placed, for the most part. Once the skin has healed, most pigment particles remain in the interstitial space of the tissue. Inks used for tattooing resist elimination by virtue of their inertness and the relatively large size of the insoluble pigment particles. A tattoo produced in this manner will partially fade over time and will generally remain present throughout the Life of the tattooed person.

Tattoos are used for a variety of reasons, primarily for ornamentation of the skin. While tattoos have traditionally been applied as designs for the skin, they are also used for permanent cosmetics, such as eyeliner and lip color often by people who cannot apply makeup, such as those suffering from arthritis or Parkinson's Disease. Additionally, for breast reconstruction after mastectomy, it is desirable to reconstruct the nipple and areola area with darker flesh tone tattooing in order to produce a natural-looking breast. Moreover, tattooing has been used to treat hypo- and hyper-pigmentation caused by vitiligo, skin grafts, port-wine stains, and other dermatologic conditions.

In all types of conventional tattooing (decorative, cosmetic, and reconstructive), once the pigment or dye has been administered into the dermis to form a tattoo, the pigment or dye generally remains permanently in place. However, many people have a change of heart after being tattooed. For example, a person may desire to remove or change the design of a decorative tattoo. Alternatively, an individual with cosmetic tattooing, such as eyeliners, eyebrows, or lip coloring, may wish to change the color or area tattooed as fashion changes. In addition, following breast reconstruction, the geometry of the breast may change over time, leading to a tattooed nipple changing from an aesthetically pleasing position to an unpleasant one.

Unfortunately, there is currently no simple and successful way to remove tattoos. Removal by surgical excision, dermabrasion, or salabrasion requires invasive procedures associated with potential complications, such as infections, and usually results in conspicuous scarring. Removal by laser therapy is the most common technique and is usually limited to eliminating only from 50–70% of the tattoo pigment, resulting in a residual smudge. Laser removal requires multiple treatment sessions (usually five to twenty) with expensive equipment for maximal elimination. Thus, the overall cost of laser removal is generally prohibitively expensive.

Additionally, most tattooing inks are made of pigments which have a wide range of particle size. If the pigment particles are small, they may diffuse through the tissues, causing "bleeding" of the color, "blurring" of the lines of the tattoo, or partial fading of the tattoo.

Temporary substitutes for tattoos are unsatisfactory because they are very short-lived. If only the surface of the skin is colored, such as by a decalcomania-containing ink (henna tattoos) or by painting on the skin, the ornamentation is easily removed by wetting or rubbing the skin or by the natural sloughing of epidermis every three to four weeks. While this technique produces only temporary skin ornamentation, it would be desirable to have the option to color the skin to last longer than a few hours, days, or weeks.

Currently, the only other means to induce temporary color design on the skin is by selective tanning, such as disclosed in French patent 2,705,615 and German patent No. 3420867. However, unless the skin is repeatedly subjected to ultraviolet radiation to maintain the tan color of the skin, the color differentiation soon fades. Additionally, there is the danger of melanoma from exposure of the skin to ultraviolet light, and tanning is now highly discouraged.

There would be a significant advantage in being able to apply a stable, indefinitely lasting tattoo while still having the means to remove the tattoo on demand with a simple, non-invasive treatment which results in complete removal of the tattoo without scarring. In addition, it would be advantageous to have available for conventional tattoing a tattoo ink which did not become blurred or partially faded over time.

SUMMARY OF THE INVENTION

It is an object of the present invention to overcome the aforesaid deficiencies in the prior art.

It is an object of the present invention to provide novel tattoo inks.

It is a further object of the present invention to produce a tattoo ink which can produce tattoos that can remain indefinitely or which can be removed on demand, i.e., erasable tattoos.

It is another object of the present invention to produce a tattoo ink which yields semi-permanent tattoos, i.e., tattoos that disappear after a predetermined period of time.

It is another object of the present invention to provide a method for erasing a tattoo.

It is another object of the present invention to provide a method for producing a tattoo in the skin which disappears after a predetermined period of time.

It is another object of the present invention to provide a method for producing a tattoo that disappears upon imposition of exogenous energy.

It is another object of the present invention to provide improved tattoo inks that have reduced blurring.

It is another object of the present invention for producing a tattoo with pigments or dyes that were previously considered unsuitable for producing a tattoo.

According to the present invention, pigments or dyes are combined with vehicles which retain the pigment or dye in the tissue, either indefinitely, or for a predetermined period of time, or until it is desired to erase the tattoo. Depending upon the vehicle employed, the pigment/vehicle complexes can be used to:

(a) make currently available tattoo inks less diffusible;

(b) convert unsuitable pigments into suitable pigment complexes;

(c) make tattoos semi-permanent; or (d) make tattoos erasable.

Tattoo Pigment Vehicles

According to the present invention, pigments or dyes are entrapped, encased, incorporated, complexed, or encapsulated in microstructures (hereinafter also referred to as "tattoo pigment vehicles") to form pigment/vehicle complexes. For the purpose of the present invention, the terms "dye" and "pigment" are interchangeable with respect to preparing tattoo inks. These pigment/vehicle complexes form a tattoo ink which can be used in any conventional tattooing process. As noted above, the tattoo pigment vehicles can be formulated so that they remain indefinitely in the dermis, so that they spontaneously disappear after a predetermined period of time, or they can be caused to disappear by imposition of an exogenous force.

The tattoo pigment/vehicle complexes can be formulated to resist spontaneous elimination from the dermis by virtue of their inherent physical characteristics, e.g., they are too large to be spontaneously eliminated; or an anchoring system anchors the pigment/vehicle system to the surrounding dermal tissue, e.g., by chemical bonding or by encapsulation into dermal cells.

Figure 1A:
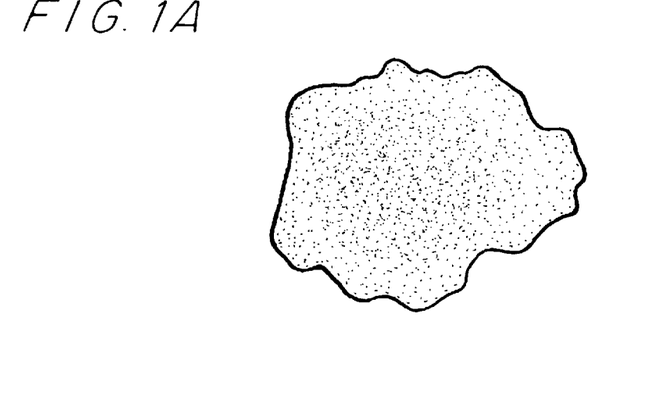
Figure 1B:
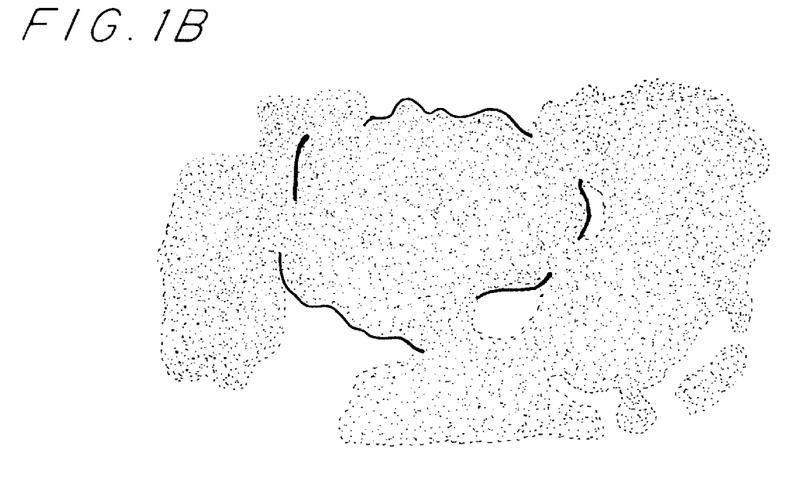
Figure 1C:
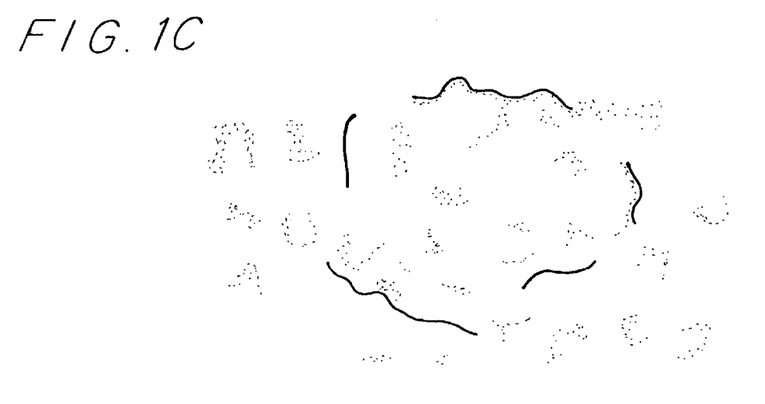

Alternatively, the vehicle materials are selected so that the pigment/vehicle complexes spontaneously disappear, such as by bioabsorption, bioerosion, or biodegradation, after a predetermined period of time (semipermanent tattoos) (FIG. 1).

Alternatively, the tattoo pigment vehicle is designed to be susceptible to a specific externally applied energy source, such as thermal, sonic (including ultrasound), light (e.g., laser, infrared, or ultraviolet light), electric, magnetic, chemical, enzymatic, mechanical (shear force from rubbing or massaging), or any other type of energy or combination of energies. In this case, also, the pigment must be of such a size that it is readily eliminated from the dermis once the vehicle is altered. Treatment of the tattooed skin with the appropriate energy source sufficiently alters the tattoo pigment vehicle, causing the vehicle to release the pigment, allowing its elimination, and thus erasing the tattoo on demand (erasable tattoos) (FIG. 1).

The tattoo pigment vehicles are composed of materials which are sufficiently translucent or transparent so as to permit the color of the entrapped pigment to show through and be visible. The various possible morphologies of the tattoo pigment vehicles include but are not limited to microspheres, microcapsules, microflakes, microparticles and coated pigment particles (FIG. 2). The tattoo pigment vehicles have a predefined size range so that they form clear, well-defined tattoos.

By entrapping, encasing, incorporating, complexing, or encapsulating pigments or dyes into tattoo pigment vehicles, the pigments or dyes are retained indefinitely in the tissue. Since the present invention contemplates the combination of a tattoo pigment vehicle with a pigment or dye, virtually any pigmented or colored substance can be used with the tattoo pigment vehicle of the present invention, including commonly used conventional tattoo inks or substances that might otherwise be considered unsuitable as a tattoo ink due to their spontaneous rapid elimination from the dermis (e.g., water soluble pigments).

The amount of pigment or dye used with the tattoo pigment vehicle depends upon the color and intensity of the pigment or dye, as well as the color and texture of the skin to which the pigment or dye is to be administered. One skilled in the art can, without undue experimentation, readily discern how much of a particular pigment must be used with a particular vehicle to obtain the desired tattoo effect.

The tattoo ink can itself be the pigment vehicle. The vehicle can be a colored particle which can be, optionally, physically or chemically modified to remain in the dermis indefinitely. Alternatively, these pigmented vehicles can be designed to spontaneously dissolve or to be bioabsorbed, causing them to disappear after a predetermined time period to form a semi-permanent tattoo. In other embodiments, these pigment vehicles composed of the pigment are such that they are susceptible to a specific externally applied energy source, such as thermal, sonic (ultrasound), light (e.g., laser light, infrared light, or ultraviolet light), electric, magnetic, chemical, enzymatic, mechanical, or any other type of energy or combination of energies. Treatment of the tattooed skin with the appropriate energy source sufficiently alters the tattoo pigment physically or chemically, allowing its elimination and, thus, erasing the tattoo on demand (FIG. 1).

Improved Tattoo Inks

Improved Conventional Inks

In one embodiment of the present invention, an improved tattoo ink is provided by incorporating conventional tattoo pigments, such as India ink, into tattoo pigment vehicles to yield a tattoo ink which has pigment particles which are more homogeneous in size and of sufficient diameter. Small particles in conventional tattoo inks, i.e., about 0.1 to 5 microns, can diffuse or migrate into surrounding tissues and cause blurring of the lines of the tattoos made. Therefore, combining the pigment with the vehicle provides particle complexes which are larger than conventional tattoo ink particles, and these larger particles do not diffuse into adjacent tissues. Additionally, the size of the vehicles can be chosen to keep the size of the pigment/vehicle complexes within a certain predetermined size range, again minimizing blurring of the lines of the tattoo.

Novel Pigments

In another embodiment of the present invention, tattoo inks are provided which permanently retain a variety of pigments in the dermis that, because of their physical characteristics, would otherwise be readily eliminated from the dermis. Elimination of such pigments is either passive (i.e., diffusing through the interstitium) or active through the complex processes of the immune system. These pigments can be retained in the dermis by entrapping, encasing, complexing, or encapsulating the pigments with the tattoo pigment vehicle. The pigment/vehicle complex so produced possesses a visible color, as well as the necessary physical characteristics to be retained indefinitely in the dermis in a manner similar to conventional tattoo pigments. In essence, the production of such a pigment/vehicle complex makes it possible to use a wide variety of pigments or dyes, including pigments previously considered unsuitable to be used as tattoo inks. Thus, virtually any pigment or colored substance can be combined with a pigment vehicle to form a complex which can be used to produce a tattoo.

In addition to increasing the variety of pigment colors available for tattooing, the tattoo pigment vehicles expand the effects that can be obtained from tattooing. For example, fluorescent pigments (such as those that are visible only when illuminated with ultraviolet or infrared light) or phosphorescent "glow-in-the-dark" pigment, which phosphoresce for a period of time after illumination, are entrapped, encased, incorporated, complexed, encapsulated, or otherwise associated with a vehicle to produce tattoo inks which fluoresce or phosphoresce, respectively.

Erasable Tattoo Inks

In another embodiment of the present invention, tattoo inks are provided which can remain indefinitely in the dermis, similar to conventional tattoo inks. However, due to the specific characteristics of the tattoo pigment vehicle, tattoos made with these inks are removable on demand, i.e., erasable. Tattoos made with these tattoo inks can be completely removed, without scarring, by applying a specific exogenous energy, such as thermal, sonic (including subsonic and ultrasonic), light (including laser light, infrared light, or ultraviolet light), electric, magnetic, chemical, enzymatic, mechanical (shear force from vibrating, rubbing, or massaging), alone or in combination, or any other type of energy or combination of energies that release the pigment or dye from the tattoo pigment vehicle (FIG. 1A).

Erasable tattoo inks are produced by entrapping, encasing, complexing, incorporating, encapsulating, or otherwise associating the desired pigments into or with tattoo pigment vehicles which are engineered to maintain the pigment in the dermis indefinitely until exposed to at least one specific exogenous energy, such as one of those enumerated above. Pigments are selected from those that are readily eliminated when in place by themselves (i.e., with no tattoo pigment vehicle) in the dermis. Exposure to the specific exogenous energy alters the tattoo pigment vehicle, releasing the entrapped pigment from the tattoo pigment vehicle and allowing the spontaneous elimination of the pigment from the dermis. Tattoos made with these pigment/vehicle complexes are "erasable" because of the unique susceptibility of the vehicle to a specific treatment applied to the tattooed skin when the individual wishes to remove the tattoo.

Semi-Permanent Tattoo Inks

In another embodiment of the present invention, tattoo inks are provided which remain in the dermis for a predetermined period of time (e.g., 3, 6, 9, months; 1, 2, 5, or 10 years; etc.), after which time the tattoo spontaneously disappears. These "semi-permanent" or "temporary" tattoo inks are produced by entrapping, encasing, complexing, incorporating, encapsulating, or otherwise associating appropriate pigments (i.e., pigments that are readily eliminated when present by themselves in the dermis) into or with tattoo pigment vehicles which slowly degrade, erode, absorb, or dissolve over a period of time. The tattoo pigment vehicle can release the entrapped pigments continuously over a predetermined period of time, such as at a constant rate slowly over a five-year period. In another morphology or composition, the vehicle releases the pigments over a short period of time once a specific percentage of the tattoo pigment vehicle has been removed from the complex. For example, a vehicle can be designed so that all of the pigment is released between the fourth and fifth years.

One example of a tattoo pigment vehicle which releases the pigment continuously over a predetermined period is one in which the pigment is incorporated or mixed homogeneously throughout the entire substance of the tattoo pigment vehicle to form the complexes. When these complexes are introduced into the dermis in the form of a tattoo, the tattoo pigment vehicle slowly bioabsorbs, releasing the pigment from the dissolving tattoo pigment vehicle material, so that the pigment is eliminated from the dermis. When all of the vehicles have been absorbed, the tattoo disappears.

To release the pigment over a short period of time, bioabsorbable microcapsules or microflakes are used as the tattoo pigment vehicle. With microcapsules, complexes comprise a core of pigment surrounded by the tattoo pigment vehicle, which maintains its integrity until a certain threshold percentage of the tattoo pigment vehicle is degraded, dissolved, eroded, or absorbed. At this point, the tattoo pigment vehicle no longer protects the pigment from elimination. The pigment is released into the dermis, where it is eliminated over a relatively short period of time.

Alternatively, microflakes comprising pigment and tattoo pigment vehicle, in which the pigment is mixed throughout the microflakes, maintain a relatively consistent pigmented surface area during the process of bioabsorption. Over a predetermined period of time, the visible pigmented surface dissolves, similar to the melting of a frozen lake or pond.

Vehicle

The tattoo pigment vehicle can comprise any substance that is biologically tolerated. As noted above, the type of tattoo pigment vehicle is chosen based upon the type of tattoo desired, either permanent, semi-permanent, or erasable. For producing permanent tattoos, the tattoo pigment vehicle comprises any biologically tolerated material which retains the pigment or dye in the dermis. For a semi-permanent tattoo, the tattoo pigment vehicle comprises a biologically tolerated material which is alterable or bioabsorbable. For an erasable tattoo, the tattoo pigment vehicle comprises a biologically tolerated material which is alterable. In any of these cases, the tattoo pigment vehicle carries a colored pigment or dye which can be administered into the dermis in any pattern or configuration in a manner identical to conventional tattooing. The tattoo pigment vehicle is sufficiently transparent or translucent so as to permit the color of the pigment or dye to show through and be visible (FIGS. 2A–2E).

BRIEF DESCRIPTION OF THE DRAWINGS

FIG. 1 shows a pigment/vehicle complex (FIG. 1A), a ruptured pigment/vehicle complex (FIG. 1B), and a ruptured complex from which the pigment has been eliminated (FIG. 1C).

FIG. 2 shows varying shapes of pigment vehicles (FIGS. 2A–2E).

DETAILED DESCRIPTION OF THE INVENTION

According to the present invention, tattooing inks are provided comprising the combination of a pigment or dye with a vehicle in such a fashion that the retention of the pigment in the tissue is carefully controlled and predictable. Conventional pigment, such as India ink, may slowly dissipate or diffuse into surrounding tissue to make the tattoo appear faded or blurry. Retention of the pigment by associating the pigment with tattoo pigment vehicles yields improved tattoos which remain distinct and do not fade or become blurred over time.

In addition, retention of novel pigments or dyes, which by themselves do not possess the necessary physical characteristics to be retained in tissue, can be associated with tattoo pigment vehicles to produce a pigment/vehicle complex which is retained in the dermis. Thus, the tattoo pigment vehicles render any pigment or dye suitable for use in tattoo ink. In addition, unconventional substances, such as fluorescent pigments (particularly those which are visible only when illuminated with ultraviolet or infrared light) or phosphorescent "glow-in-the-dark" pigments, which emit light for a period of time after being illuminated, can be retained in the dermis by entrapment, encasement, incorporation, complexing, or encapsulation by tattoo pigment vehicles to produce tattoo inks which fluoresce or phosphoresce, respectively.

When it is desired to produce erasable tattoos, the tattoo pigment vehicle is made of a material that disrupts and releases the pigment or dye upon imposition of an external energy, such as thermal, sonic, light, electric, magnetic, chemical, enzymatic, mechanical, combinations thereof, or any other type of energy or combination of energies that can be used to disrupt the tattoo pigment vehicle.

Alternatively, to produce "semi-permanent" or "temporary" tattoos, the tattoo pigment vehicle is made of a material that slowly dissolves, bioerodes, bioabsorbs, or biodegrades in the dermis without the imposition of an exogenous energy. Upon spontaneous disruption, bioabsorption, bioerosion, or biodegradation of the tattoo pigment vehicle, the pigment is released and spontaneously eliminated.

The tattoo pigment vehicles used to retain the pigments or dyes are biologically tolerated and form pigment/vehicle complexes that are sufficiently large or immunoprotected that the pigment/vehicle complexes are not readily eliminated from the dermis. Alternatively, the tattoo pigment vehicle resists elimination from the dermis by chemical bonding to dermal elements or by being encapsulated in cellular elements of the dermis. The color-carrying particles can be injected by any conventional tattooing means, including those described in U.S. Pat. Nos. 5,472,449; 4,798,582; 5,582,473; and 5,054,339.

I. Tattoo Pigment Vehicles

The tattoo pigment vehicles are used to encapsulate, entrap, encase, complex, or otherwise incorporate pigments or dyes. These tattoo pigment vehicles are biologically tolerated and form color-carrying particles that possess specific characteristics necessary for the type of tattoo ink desired. For permanent tattoos, the tattoo pigment vehicles are designed to remain indefinitely in the dermis to prevent the pigment/vehicle complex from being readily eliminated from the dermis. The tattoo pigment vehicles resist spontaneous elimination from the dermis by the nature of their inherent physical characteristics (e.g., large size), by immunoprotection (e.g., "stealth" technology using polyethylene glycol incorporation), or by an anchoring system which anchors the vehicle to the dermal tissue (e.g., chemical bonding or encapsulation into dermal cells). These pigment/vehicle complexes are used to form a tattoo ink which can be used in any conventional tattooing process.

The tattoo pigment/vehicle complexes are preferably from about 1 to 700 microns in diameter, and more preferably from about 5 to about 300 microns in diameter. Particles of this size produce clear tattoos with little or no diffusion of the pigment to cause blurring of the lines. The size of the tattoo pigment/vehicle complex is not of functional significance if an anchoring system is used to prevent spontaneous elimination or diffusion. That is, any size tattoo pigment/vehicle complex is useable if the vehicle resists spontaneous elimination secondary to chemical bonding to the surrounding tissue, or if the complex is entrapped within cells.

Figure 2A:
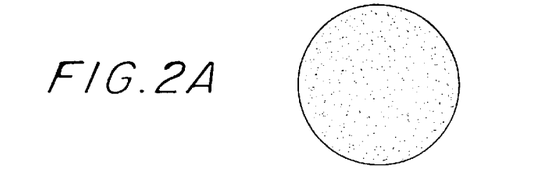
Figure 2B:
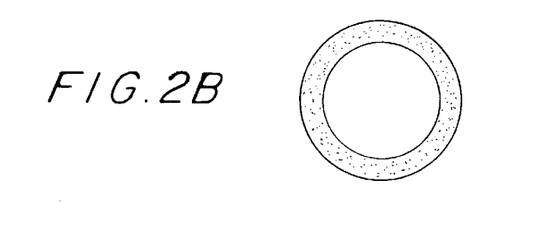
Figure 2C:
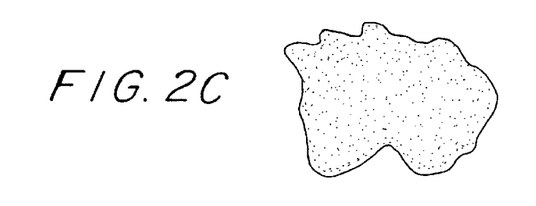
Figure 2D:
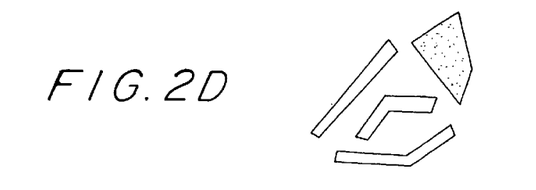
Figure 2E:
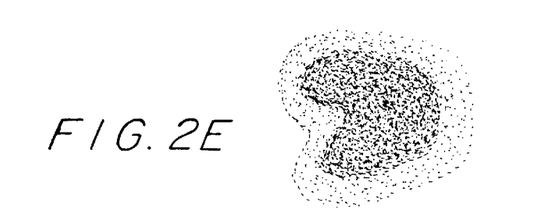

The various possible morphologies of the tattoo pigment/vehicle complexes include, but are not limited to, microspheres (FIG. 2A), microcapsules (FIG. 2B), microflakes (FIG. 2D), microparticles (FIG. 2C), liposomes, and coated pigment particles (FIG. 2E). The specific geometry of the pigment/vehicle complex influences the amount of pigment or dye required to produce the desired effect. Thin-shelled microcapsules have a small percentage of polymer, generally about 0.5% or more, while solid microspheres or flakes may have a much higher percentage of polymer, in excess of 80% or more. The amount of pigment or dye, as well as the morphology of the vehicle, can be varied depending upon the color of the pigment or dye and the color of the skin on which the tattoo ink is to be used. One skilled in the art of preparing tattoo inks can readily determine without undue experimentation how much pigment or dye is required for each type of pigment/vehicle complex to produce the desired effect when administered into the dermis.

When the vehicle is in the form of microspheres, shown in FIG. 2A, the microspheres can be either solid or hollow. The microspheres contain the pigment or dye either throughout the substance of the vehicle, only in the internal portion of the vehicle, or only in the external portion of the vehicle. If the pigment or dye is contained only in the internal portion of the vehicle, the overlying portion must be sufficiently translucent or transparent to permit the pigment or dye color to be visible. The microspheres possess specific characteristics, primarily size and immunoprotection, which resist and prevent spontaneous elimination from the dermis.

Microcapsules, shown in FIG. 2B, are microspheres with an outer shell and a central cavity or core. The outer shell of the microcapsule is composed of a selected material with the desired stability characteristics, while the central cavity or core contains the pigment or dye. of course, when the microcapsules are used to produce a permanent tattoo ink, the central cavity can contain the carrier and the outer shell can comprise the pigment or dye.

The microcapsules can be constructed using methods known to those skilled in the art. For example, spheres can be formed by interfacial polymerization, hot melt microencapsulation, rotating cylinders or disks, solvent removal, solvent evaporation, or other methods known to those skilled in the art, including those disclosed in U.S. Pat. No. 4,898,734 to Mathiowitz et al. and No. 5,254,428 to Ishjikawa et al.

For example, polyamide microcapsules can be constructed by interfacial polymerization using the method of Mathiowitz et al. in *J. App. Poly. Sci.*, 26:809 (1981). In this method, an aqueous solution of the amine and polyvinyl alcohol along with the pigment to be encapsulated are added to a suspension of a benzene:xylene solution (2:1, v/v) of the dichloride in water. Azobisisobutyronitrile and/or azobenzene are added to the organic solution. The polycondensation reaction is allowed to continue for a desired period of time. Microcapsules are separated by decantation, repeatedly washed with distilled water, and dried by rapid washing with acetone.

The tattoo pigment/vehicle complexes can also be produced in the form of microflakes, FIG. 2D, small flat flakes of a selected material with the desired stability and physical characteristics. The pigment or dye is mixed throughout the substance of the microflakes. This tattoo pigment/vehicle complex morphology yields a larger surface to volume ratio as compared to microspheres, microcapsules, or microparticles. As the vehicle degrades, dissolves, absorbs, or erodes, the gross appearance of the flakes is relatively unaffected. Once a high percentage of the original material has eroded, only then does the gross appearance fade noticeably.

The tattoo pigment/vehicles are also produced as coated particles, FIG. 2E. The selected pigment or dye is coated using any conventional technique with a material which encases the pigment, yielding a colored particle (pigment/vehicle complex) with characteristics which prevent spontaneous elimination from the dermis. If an erasable tattoo is desired, the coating material is one which is altered when a specific energy is applied. This causes the coating material to disrupt, allowing the pigment to be spontaneously eliminated. Alternatively, if a semi-permanent tattoo is desired, the coating material is one which bioabsorbs, bioerodes, dissolves, or biodegrades over a period of time, releasing the pigment for its eventual elimination.

The tattooing pigments or dyes can also be encapsulated in liposomes, such as those described in U.S. Pat. No.

4,900,556 to Wheatly et al. Liposomes are highly advanced assemblages consisting of concentric closed membranes formed by water-insoluble polar lipids, particularly phospholipids. Other substances, such as cholesterol, can be included in the membrane. The stability, rigidity, and permeability of the liposomes are altered by changes in the phospholipid composition. Membrane fluidity is generally controlled by the composition of the fatty acyl chains of the lipid molecules. The fatty acyl chains can exist in an ordered, rigid state or in a relatively disordered fluid state. Factors affecting rigidity include chain length, degree of saturation of the fatty acyl chains and temperature. Larger chains interact more strongly with each other, so fluidity is greater with shorter chains. Saturated chains are more flexible than unsaturated chains. Transition of the membrane from the rigid to the fluid state occurs as the temperature is raised above the "melting temperature." The melting temperature is a function of the length and degree of unsaturation of the fatty acyl chain.

Additionally, inclusion of a sterol, such as cholesterol, or a charged amphiphile, can alter the stability, rigidity, and permeability of the liposome by altering the charge on the surface of the liposome and increasing the distance between the lipid bilayers. Proteins and carbohydrates may be incorporated into the liposomes to further modify their properties.

Liposomes are conventionally prepared by dissolving an appropriate concentration of phospholipid in an organic solvent, evaporating the solvent, and subsequently disrupting the dry lipid layer with excess water or buffer. The pigments or dyes can be entrapped within the liposomes during formation. "Entrapment" means the incorporation of the pigment or dye in the lipid framework of the bilayer or the passive encapsulation of the pigment or dye in the aqueous compartments.

The liposomes can be designed to degrade upon exposure to a particular stimulus, such as light, heat, or sonic energy. Liposomes which undergo dramatic increases in permeability when irradiated with light are known. Examples of these photosensitive phospholipids are 1,2-diretinoyl-Sn-glycero-3-phosphocholine and 1-palmitoyl,2-retinoyl-Sn-glycero-3-phosphocholine. The permeability of liposomes formed from either or both of these phospholipids is directly proportional to temperature. Upon exposure to 30 to 120 seconds of 360 nm light, the permeability of the liposomes increases dramatically, from approximately 20% to almost 90%. Thus, pigments or dyes encapsulated within such liposomes can be administered into the dermis to produce a relatively permanent tattoo. When the owner of the tattoo wishes to erase the tattoo, the owner merely exposes the tattoo to from about 30 to 120 seconds of light at about 360 nm, and the liposomes become permeable, releasing the dye or pigment into the body from which the dye or pigment is slowly eliminated.

The vehicle material can be any biocompatible material that possesses the in vivo characteristics required for the type of tattoo to be created. Thus for permanent tattoos, the vehicle material is substantially inert and resists elimination, remaining indefinitely in the dermis. For erasable tattoos, the vehicle material must be capable of releasing the pigment on demand upon imposition of a specific exogenous energy. For semi-permanent tattoos, the vehicle material must be bioabsorbable, bioerodable, or biodegradable over a predetermined period of time.

Among other materials that can function as tattoo pigment vehicles in the present invention are those which the FDA has found acceptable for use as food additives, including succinylated gelatin, arabinogalactan, glutaraldehyde, petroleum wax, and mixtures thereof. Additional materials for use as tattoo pigment vehicles, according to the present invention, include poloxanele, poly(acrylic acid co-hypophosphorite) sodium salt, polyacrylamide, alginate/alginic acid, calcium caseinate, calcium polypectate, cellulose acetate phthalate, cellulose acetate trimellitate, chitosan, edible and natural waxes, fatty acids, fatty alcohols, gellan gums, hydroxy cellulose, hydroxy ethyl cellulose, hydroxy methyl cellulose, hydroxy propyl cellulose, hydro propyl ethyl cellulose, hydroxy propyl methyl cellulose phthalate, lipids, mono-, di- and triglycerides, pectins, phospholipids, polyalkyl($C_{16}$–$C_{22}$) acrylate, polyethylene, oxidized polyethylene, polyethyleneimine reacted with 1,2-dichloroethane, polyoxyethylene (600)dioleate, polyoxyethylene(600)monoricinoleate, polyoxyethylene(23)lauryl ether, polyethylene glycol, polyethylene glycol(400)dioleate, polyethylene glycol(400) mono-& di-oleate, polyglycerol esters of fatty acids, polyisobutylene, polyglycerol phthalate ester of coconut oil fatty acids, polymaleic acid and/or its sodium salts, polyoxyethylene glycol(400)mono-& di-oleates, polyoxyethylene(23)lauryl ether, polyoxyethylene(40) monostearate, polyoxyethylene -poyoxypropylene block polymers, polyoxyethylene (20)sorbitan monooleate, polyoxyethylene(20)sorbitan monostearate, polyoxyethylene(2)sorbitan tristearate, polyoxypropylene glycol, polyvinyl acetate, polysorbate 80, polyvinylpolypyrrolidone, polyvinylpyrrolidone, and poly (20 vinylpyridine-co-styrene).

Other materials for forming the tattoo pigment vehicles are biologically tolerated, and include but are not limited to waxes, polyolefins, or paraffins (e.g., Bayberry, spermaceti, Japan, Ross, etc.), triglycerides, phospholipids, fatty acids and esters thereof (e.g., lauric acid, palmitic acid, sorbitan monopalmitate, sorbitan monostearate, etc.), poly(vinyl palmitate), poly(hexadecyl acrylamide), poly(butyl acrylate), poly(hexadecyl acrylate), poly(octadecyl acrylate), poly(dodecene), poly(isobutene), poly(trimethyl glutarate), polyanhydides, polyorthoesters, polystyrene, polyurethane, polypropylene, polymethacrylate, polytetrafluoroethylene, and other known polymers, ceramics, or glasses.

The amount of pigment or dye used with the tattoo pigment vehicle depends upon the desired color and intensity of the pigment or dye, as well as the color and texture of the skin to which the pigment or dye is to be administered. To form tattooing ink, the tattoo pigment/vehicle complexes are formed into microstructures of desired composition and geometry and suspended in a carrier, such as ethanol or water, or any other conventional tattooing ink fluid, in a concentration sufficient to produce the desired coloration of the skin. Alternatively, the tattoo pigment/vehicle complexes are in the form of a suspension in a semi-liquid paste, similar to many conventional tattoo inks. The size of the tattoo pigment/vehicle complex is selected so that the ink is easily administered into the dermis with conventional tattoo ink devices.

To form tattoos according to the present invention, suitable pigments or dyes are used and incorporated in the tattoo pigment vehicle desired. The composition of the vehicle is selected according to whether the tattoo is to be permanent, semi-permanent, or erasable. When the tattoo is to be semi-permanent, a tattoo pigment vehicle is chosen which bioabsorbs, bioerodes, or biodegrades at the predetermined time the tattoo is to disappear spontaneously.

Any conventional pigments or dyes suitable for tattoos can be used for the color element of tattoo inks of the present invention, as well as any biologically tolerated colors. The Food and Drug Administration considers the pigments used in tattooing to be "color additives" subject to the FDA color additive regulations under the Federal Food, Drug and Cosmetic Act. [cf. 21 U.S.C. Sections 321(t) and 379(e)]. In addition, virtually any pigment or colored substance tolerated by the body can be used as an appropriate tattoo ink when incorporated with a tattoo pigment vehicle to form a pigment/vehicle complex according to the present invention.

An alternative type of tattoo pigment/vehicle complex is produced with the vehicle also comprises the pigment per se. Water soluble pigments (i.e., pigments that do not possess the necessary characteristics of remaining indefinitely in the dermis) are modified in a specific manner physically or chemically (i.e., aggregated, cross-linked) to provide the necessary characteristics to resist spontaneous elimination from the dermis. In essence, such modifications to the pigment confer upon the pigment itself the functional qualities of both tattoo pigment vehicle and the colorant. These pigments are modified to become their own tattoo pigment vehicle and, therefore, do not require a separate microstructure or composition to form a tattoo pigment/vehicle complex. Furthermore, this alternative configuration can be made so that pigment complex spontaneously disappears after a predetermined time period (semi-permanent tattoo) or is susceptible to a specific external energy, such as thermal, sonic (including ultrasonic, audible, and subsonic), light (including laser light, infrared light, or ultraviolet light), electric, magnetic, chemical, enzymatic, mechanical (such as shear force from rubbing or massaging), or any other type of energy or combination of energies. Treatment of the tattooed skin with the appropriate energy sufficiently alters the tattoo pigment vehicle physically or chemically, allowing for elimination of the pigment and thus erasing the tattoo on demand (erasable tattoo).

II. Improved Tattoo Inks

A. Improved Conventional Inks

According to the present invention, an improved tattoo ink is provided by incorporating conventional tattoo pigments (e.g., India ink) into vehicles which yield pigment/vehicle complexes that remain in the dermis by virtue of their size, attachment to dermal elements, or encapsulation by cells. In this embodiment of the invention, tattooing inks produce permanent tattoos which have clear lines by entrapping diffusible pigment particles into non-diffusible larger aggregates. Materials used for the tattoo pigment vehicle to produce permanent tattoo inks are substances which possess the physical characteristics necessary to remain in the dermis indefinitely. These tattoo pigment vehicle materials are used for producing permanent tattoos wherein all of the pigment/vehicle complexes have a sufficiently large size so that the tattoo design does not become blurred by the diffusion of the pigment into adjacent dermis. When tattoo inks contain pigmented particles only of an optimal size, generally from 1 to 500 microns, there is less blurring of the lines of the tattoo, and the pigment does not partially fade or diffuse into adjacent tissues or become eliminated from the dermis.

Alternatively, the tattoo pigment vehicle can bind to dermal elements, such as collagen, elastin, glycosaminoglycans, etc., through ionic, covalent, or other molecular mechanisms. The binding factors include, but are not limited to, natural adhesion molecules, such as fibronectin, laminin, vitronectin, fibrinogen, fibrin, intercellular adhesion molecule-1, and various documented adhesion peptide sequences, such as those containing arginine, glycine, aspartic acid sequences (RGD), other peptide sequences (such as YIGSR), or- synthetic adhesives such as cyanoacrylates.

B. Novel Pigments or Effects

In another embodiment of the present invention, tattoo inks are provided which permanently immobilize in the dermis a variety of pigments that, because of their physical characteristics, would otherwise be readily eliminated from the dermis. Elimination of such pigments is either passive (i.e., by dissolving into the interstitial fluid) or active, through the complex processes of the immune system. By entrapping, encasing, incorporating, complexing, encapsulating, or otherwise associating these pigments (which are otherwise readily eliminated if placed in the dermis themselves) with a tattoo pigment vehicle, the pigment/vehicle complex so produced possesses a visible color, as well as the necessary physical characteristics to remain indefinitely in the dermis (similar to conventional tattoo pigments). In essence, the production of such a pigment/vehicle complex or color-carrying particle allows a wide variety of pigments, including pigments not previously considered suitable, to be used as tattoo inks. Of course, these pigments may also be incorporated into vehicles which produce semi-permanent or erasable tattoos, so that the duration of the tattoo is controlled by the vehicle rather than by the pigment.

Currently, over 50 different colors and shades of pigment are used in tattooing, ranging from metallic salts, such as iron oxide and titanium dioxide, to synthetic organic dyes. Additionally, colorants obtained from natural sources, such as annatto extract, beta-carotene, B-Apo-8' carotenal, beet powder, canthazanthin, caramel color, carrot oil, cochineal extract, ferrous gluconate, grape color extract, grape skin extract, paprika, riboflavin, saffron, turmeric, and vegetable juice, can be used in the inks according to the present invention.

Additional coloring agents that may be used in preparing inks according to the present invention include color additives for use in the U.S. for foods, drugs, cosmetics, and medical devices which are enumerated in 21 C.F.R. Sections 73, 74, and 82, which are hereby incorporated by reference in their entirety.

Because the tattoo pigment vehicles of the present invention may be destined to encapsulate the pigments or dyes before they are administered to the dermis, the tattoo inks of the present invention may reduce the toxicity or allergenicity, and, thus, pigments or dyes other than those traditionally used in tattoos may be used in the inks according to the present invention.

In addition to increasing the variety of pigment colors available for tattooing, as virtually any pigment or colored substance could be used for tattooing, the tattoo pigment vehicles expand the effects that can be obtained from tattooing. For example, fluorescent pigments (such as those that are visible only when illuminated with ultraviolet or infrared light), or phosphorescent "glow-in-the-dark" pigments, which phosphoresce for a period of time after illumination, are entrapped, encased, incorporated, complexed, or encapsulated to produce tattoo inks which fluoresce or phosphoresce, respectively.

III. Erasable Tattoo Inks

Where the tattoo is to be erasable, the tattoo pigments vehicles possess characteristics which resist spontaneous elimination from the dermis, while the pigments or dyes themselves are sufficiently small and diffusible so that they are readily eliminated from the dermis in the absence of the tattoo pigment vehicle. When an individual has a tattoo applied using the erasable tattoo ink of this invention and subsequently wishes the tattoo to be removed or erased, the tattoo pigment vehicles are disrupted, degraded, or altered by imposition of specific energy, such as thermal, sonic, light, electric, magnetic, chemical, enzymatic, mechanical, or any other type of energy or combination of energy which releases the pigment or dye from the pigment/vehicle complex allowing its elimination from the body, thus erasing the tattoo.

For example, for tattoo pigment vehicles which melt, disrupt, weaken, or degrade upon application of heat, a melting temperature of from about 40 to about 55° C. is useful. Examples of such heat-labile or meltable materials for fabrication of tattoo pigment vehicles include, but are not limited to, the following:

| Polymer | Melting Temperatures (° C.) |
| --- | --- |
| Poly hexadecylester | 43 |
| Poly-n-hexadecyl-acrylamide | 45 |
| Poly butyl ester | 47 |
| Poly-1-dodecene | 45–48 |
| Polyisobutene | 44–46 |
| Poly (hexadecyl acrylamide) | 45 |
| Poly (butyl acrylate) | 47 |
| Poly (hexadecyl acrylate) | 43 |
| Poly (octadecyl acrylate) | 56 |
| Poly (dodecne) | 45–49 |
| Poly (isobutene) | 44–46 |
| Bayberry wax | 42–48 |
| Spermaceti wax | 42–50 |
| Japan wax | 50–56 |
| Ross wax (refined parafin wax) | 48–50 |

| Polymer | Melting Temperatures (° C.) |
| --- | --- |
| Carbowax (polyethylene glycol 1450) | 43–46 |
| Lipoxol 1550 or 2000 (MED PEG-32 or 40) | 40–50 |
| Lauric acid | 44–46 |
| Palmitic acid | 59–61 |
| Sorbitan Monopalmitate | 46–47 |
| Sorbitan Monostearate | 56–58 |
| Softisan (142 or 601 glycerol esters of $C_{10-18}$ fatty acids | 40–45 |

The materials for forming the-tattoo pigment vehicles are biologically tolerated, and include, but are not limited to, waxes or paraffins, triglycerides, fatty acids and esters, poly(alkyl acrylates), polyolefins, polyurethanes, polymethacrylates, polytetrafluoroethylenes, and other known polymers, ceramics or glasses which possess the properties required for a pigment vehicle according to the present invention.

The material encasing, entrapping, incorporating, complexing, or encapsulating the pigment will, if heated to the melting temperature of the material, release the pigment, allowing its elimination from the dermis.

When liposomes are used to produce erasable tattoo inks, the liposomes are designed to disrupt, degrade, or be altered (physically or chemically) upon exposure to a particular stimulus, such as thermal, sonic (ultrasound), light (e.g., laser light, infrared light, ultraviolet light), electric, magnetic, chemical, enzymatic, mechanical (shear force from vibrating, rubbing, or massaging), or any other type of energy or combination of energies. This specific stimulus releases the pigment or dye from the liposome to be subsequently spontaneously eliminated from the body.

Liposomes which undergo dramatic increases in permeability when irradiated with light are known. Examples of these photosensitive phospholipids are 1,2-diretinoyl-Sn-glycer-3-phosphocholine and 1-palmitoyl, 2-retinoyl-Sn-glycero-3-phosphocholine. The permeability of liposomes formed from either or both of these phospholipids is directly proportional to temperature. Upon exposed to 30 to 120 seconds of 360 nm light, the permeability of the liposomes increases dramatically, from approximately 20% to almost 90%. Thus, pigments or dyes encapsulated within such liposomes can be administered into the dermis to produce a relatively permanent tattoo. When the owner of the tattoo wishes to erase the tattoo, the owner merely exposes the tattoo to from about 30 to 120 seconds of light at about 360 nm, and the liposomes become permeable, releasing the dye or pigment into the body, from which the dye or pigment is slowly eliminated.

Another photosensitive system is described by Kano et al. (1981a and 1981b). Kano et al. showed that incorporation of light isomerizable azobenzene lipids into liposome membranes produces vesicles with increased membrane permeability upon exposure to light.

As with polymer and wax vehicles, some liposomes are temperature sensitive. Specific lipid composition are formulated so that their transition temperature is above the temperature at which the liposomes are to store the pigment or dye, i.e., above body temperature, yet low enough to allow for release when the temperature is raised to a degree not harmful to the body for the period of time required. In this case, pigments or dyes are encapsulated in the liposomes and administered into the dermis as for conventional, permanent, tattoos. If and when the owner of this type of tattoo wishes to remove the tattoo, a heat source (such as a heating pad) is applied to the skin in the vicinity of the tattoo, altering the permeability of or rupturing the liposomes and thereby releasing the pigment or dye to be eliminated from the dermis.

Other stimuli and methods for preparing liposomes which are responsive to stimuli and which are characterized by a particular rigidity, permeability, and stability are known to those skilled in the art. Essentially, any method for preparing liposomes which become unstable after a predetermined period of time or whose permeability or stability can be significantly altered by manipulation of the immediate environment can be used to produce semi-permanent or erasable tattoos.

IV. Semi-Permanent Tattoo Inks

In another embodiment of the present invention, tattoo inks are provided which remain in the dermis for a predetermined period of time (e.g., 3, 6, 9, months or 1, 2, 5, 10 years, etc.) and then spontaneously disappear. These "semi-permanent" or "temporary" tattoo inks are produced by entrapping, encasing, completing, incorporating, or encapsulating appropriate pigments (pigments which are readily eliminated when present by themselves in the dermis) into tattoo pigment vehicles which slowly bioabsorb, bioerode, or biodegrade over a predetermined period of time, such as at a constant rate slowly over a five-year period, or can release the pigments over a short period of time once a specific percentage of the tattoo pigment vehicle has been absorbed. For example, all of the pigment may be released between the fourth and fifth years.

One example of a tattoo pigment vehicle which releases the pigment continuously over a predetermined period is one in which the pigment is incorporated or mixed in throughout the entire substance of the tattoo pigment vehicle to form color-carrying particles. When these pigment/vehicle complexes are introduced into the dermis (in the form of a tattoo), the tattoo pigment vehicle slowly bioabsorbs, releasing the pigment from the dissolving tattoo pigment vehicle maturely, eliminating the pigment from the dermis. When all of the pigment/vehicle complexes have been absorbed, the tattoo is no longer visible.

To release the pigment over a short period of time, bioabsorbable microcapsules or microflakes are used as the tattoo pigment vehicle. With microcapsules, pigment/vehicle complexes comprise a core of pigment surrounded by the tattoo pigment vehicle, which maintains its integrity until a certain threshold percentage of the tattoo pigment vehicle is dissolved, bioeroded, or bioabsorbed. At this point, the tattoo pigment vehicle no longer protects the pigment from elimination. The pigment is released into the dermis, where it is eliminated over a relatively short period of time.

Alternatively, microflakes made of pigment and tattoo pigment vehicle, in which the pigment is mixed throughout the microflakes, maintain a relatively consistent pigmented surface area during the process of bioabsorption. Over a predetermined period of time, the visible pigmented surface dissolves, similar to the melting of a frozen lake or pond.

The tattoo pigment vehicle for the pigment or dye comprises any biologically tolerated material that retains the pigment or dye in the dermis, for whatever time or under whatever conditions are desired. In any of these cases, the tattoo pigment vehicle carries a colored pigment or dye which can be administered into the dermis in any pattern or configuration in a manner similar to conventional tattooing. The tattoo pigment vehicle is sufficiently transparent or translucent so as to permit the color of the pigment or dye to show through and be visible. Preferably, the pigment or dye comprises particles smaller than 1 micron.

For producing semi-permanent tattoos, the pigments or dyes are entrapped, encased, complexed, incorporated, encapsulated, or otherwise associated in or with tattoo pigment vehicles composed of bioabsorbable, bioerodable, or biodegradable material. The material is designed to bioabsorb, bioerode, or biodegrade over a predetermined period of time so that the tattoo ink, when administered into the dermis, creates a tattoo which lasts only until the tattoo pigment vehicle bioabsorbs. Upon partial or complete bioabsorption of the tattoo pigment vehicle, the pigment or dye is released, allowing its elimination from the dermis.

A great many biodegradable polymers exist, and the length of time which the tattoo lasts in a visible state in the dermis is determined by controlling the type of material and composition of the tattoo pigment vehicle. Among the bioabsorbable, bioerodable, or biodegradable polymers which can be used are those disclosed in Higuchi et al., U.S. Pat. Nos. 3,981,303, 3,986,510, and 3,995,635, including zinc alginate poly(lactic acid), poly(vinyl alcohol), polyanhydrides, and poly(glycolic acid). Alternatively, microporous polymers are suitable, including those disclosed in Wong, U.S. Pat. No. 4,853,224, such as polyesters and polyethers, and Kaufman, U.S. Pat. Nos. 4,765,846 and 4,882,150.

Other polymers which degrade slowly in vivo are disclosed in Davis et al., U.S. Pat. No. 5,384,333, which are biodegradable polymers which are solid at 20–37° C. and are flowable, e.g., a liquid, in the temperature range of 38–52° C. In preparing a semi-permanent tattoo, the dye or pigment is incorporated in the polymer matrix, and the system can be warmed to approximately 50° C., where it liquifies. The system is then injected into the dermis in a desired tattoo design, where it cools and resolidifies.

For this type of semi-permanent tattoo pigment vehicle, any biodegradable polymer system which has the following characteristics can be used, including homopolymers, copolymers, block copolymers, waxes and gels, as well as mixtures thereof. A preferred polymer system is a triblock copolymer of the general formula

A-B-A where A represents a hydrophobic polymer block, and B represents a hydrophilic polymer. The monomers and polymers are preferably linked through ester groups. Preferred hydrophobic polymers and oligomers include, but are not limited to, units selected from polyglycolic acid, polyethylene terephthalate, polybutyl lactone, polycaprolactone, D-polylactic acid, polytetrafluoroethylene, polyolefins, polyethylene oxide, polylactic acid, polyglutamic acid, poly-L-lysine, and poly-L-aspartic acid. Preferred hydrophilic polymers include polyethylene glycol, polypropylene glycol, and poly(vinyl alcohol).

Hydrogel matrices or tattoo pigment vehicles for preparing semi-permanent tattooing inks are formed by crosslinking a polysaccharide or a mucopolysaccharide with a protein and loading the dye or pigment into the hydrogel matrices. Proteins include both full-length proteins and polypeptide fragments, which in either case may be native, recombinantly produced, or chemically synthesized. Polysaccharides include both polysaccharides and mucopolysaccharides.

A hydrogel in which the pigment or dye can be incorporated to a tattoo ink is disclosed in Feijen, U.S. Pat. No. 5,041,292. This hydrogel comprises a protein, a polysaccharide, and a cross-linking agent providing network linkages therebetween wherein the weight ratio of polysaccharide to protein in the matrix is in the range of about 10:90 to about 90:10. The pigment or dye is mixed into this matrix in an amount sufficient to provide color when the hydrogel matrix is administered to the dermis.

Examples of suitable polysaccharides include heparin, fractionated heparins, heparan, heparan sulfate, chondroitin sulfate, and dextran, including compounds described in U.S. Pat. No. 4,060,081 to Yannas et al. Using heparin or heparin analogs is preferred because there appears to be reduced immunogenicity. The protein component of the hydrogel may be either a full-length protein or a polypeptide fragment. The protein may be in native form, recombinantly produced, or chemically synthesized. The protein composition may also be a mixture of full-length proteins and/or fragments. Typically, the protein is selected from the group consisting of albumin, casein, fibrinogen, gamma-globulin, hemoglobin, ferritin and elastin. The protein component may also be a synthetic polypeptide, such as poly (α-amino acid). polyaspartic acid or polyglutamic acid. Albumin is the preferred protein component of the matrix, as it is an endogenous material which is biodegradable in blood and tissue by proteolytic enzymes. Furthermore, albumin prevents adhesion of thrombocytes and is nontoxic and nonpyrogenic.

In forming hydrogels containing pigments or dyes; the polysaccharide or mucopolysaccharide and the protein are dissolved in an aqueous medium, followed by addition of an amide bond-forming cross-linking agent. A preferred cross-linking agent for this process is a carbodiimide, preferably the water-soluble diimide N-(3-dimethyl-aminopropyl)-N-ethylcarbodiimide. In this method, the cross-linking agent is added to an aqueous solution of the polysaccharide and protein at an acidic pH and a temperature of about 0 to 50° C., preferably from about 4 to about 37° C., and allowed to react for up to about 48 hours. The hydrogel so formed is then isolated, typically by centrifugation, and washed with a suitable solvent to remove uncoupled material.

Alternatively, a mixture of the selected polysaccharide or mucopolysaccharide and protein is treated with a cross-linking agent having at least two aldehyde groups to form Schiff-base bonds between the components. These bonds are then reduced with an appropriate reducing agent to give stable carbon-nitrogen bonds.

Once the hydrogel is formed, it is loaded with the pigment or dye by immersing the hydrogel in a solution or dispersion of the pigments or dye. The solvent is then evaporated. After equilibration, the loaded hydrogels are dried in vacuo under ambient conditions and stored.

Virtually any pigment or dye may be loaded into the hydrogel vehicles, providing that surface considerations, such as surface charge, size, geometry and hydrophilicity, are taken into account. For example, incorporation and release of a high-molecular weight dye will typically require a hydrogel having a generally lower degree of cross-linking. The release of a charged pigment or dye will be strongly influenced by the charge and charge density available in the hydrogel, as well as by the ionic strength of the surrounding media.

The rate of pigment or dye release from the vehicles can also be influenced by post-treatment of the hydrogel formulations. For example, heparin concentration at the hydrogel surface can be increased by reaction of the formulated hydrogels with activated heparin (i.e., heparin reacted with carbonyldiimidazole and saccharine) or with heparin containing one aldehyde group per molecule. A high concentration of heparin at the hydrogel surface will form an extra "barrier" for positively charged dyes or pigments at physiological pH values. Another way of accomplishing the same result is to treat the hydrogels with positively charged macromolecular compounds like protamine sulfate, polylysine, or like polymers. Another way of varying hydrogel permeability is to treat the surfaces with biodegradable block copolymers containing both hydrophilic and hydrophobic blocks. The hydrophilic block can be a positively charged polymer, like polylysine, while the hydrophilic block can be a biodegradable poly(a-amino acid), such as poly(L-alanine), poly(L-leucine), or similar polymers.

Another slow-release system used as a tattoo pigment vehicle for pigments or dyes to form a semi-permanent tattoo is a dye or pigment and an enzyme encapsulated within a microcapsule having a core formed of a polymer which is specifically degraded by the enzyme and a rate controlling skin. The integrity of the shell is lost when the core is degraded, causing a sudden release of pigment or dye from the capsule. In this type of system, the microcapsule consists of a core made up of a polymer around which there is an ionically-bound skin or shell. The integrity of the skin or shell depends on the structure of the core. An enzyme is encapsulated with the biologically-active substance to be released during manufacture of the core of the microcapsule. The enzyme is selected to degrade the core to a point at which the core can no longer maintain the integrity of the skin, so that the capsule falls apart. An example of such as system consists of an ionically cross-linked polysaccharide, calcium alginate, which is ionically coated with a polycationic skin of poly-L-lysine. The enzyme used to degrade the calcium-alginate coated with poly-L-lysine microcapsules is an alginase from the bacteria *Beneckea pelagio* or *Pseudomonas putida*. Enzymes exist that degrade most naturally-occurring polymers. For example, the capsule core may be formed of chitin for degradation with chitinase. Other natural or synthetic polymers may also be used and degraded with the appropriate enzyme, usually a hydrogenase.

A particularly preferred bioabsorbable polymer vehicle is a triblock copolymer of poly caprolactone-polyethylene glycol-poly caprolactone. This polymer contains ester bonds which hydrolyze in a hydrophilic environment. The biodegradable polymer matrix should comprise about 30–99% of the tattoo ink.

Several mechanisms are involved in the rate and extent of dye or pigment release. In the case of very high molecular weight pigments, the rate of release is more depending on the rate of tattoo pigment vehicle bioabsorption. With lower molecular weight pigments, the rate of pigment release is more dominated by diffusion. In either case, depending on the tattoo pigment vehicle composition selected, ionic exchange can also play a major role in the overall release profile.

All references cited herein are hereby incorporated herein in their entirety.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

What is claimed is:

1. A tattoo ink comprising particles comprising at least one pigment or dye and a vehicle for said pigment or dye which surrounds said pigment or dye.

2. A tattoo ink according to claim 1, wherein said particles range in size from 1 to 700 microns.

3. A tattoo ink according to claim 1, wherein said pigment or dye is selected from the group consisting of materials which are fluorescent and phosphorescent.

4. A tattoo ink according to claim 1, wherein said vehicle comprises a substance that can be altered by exposure to exogenous energy to reduce retention of the pigment or dye and permit elimination of the pigment or dye from the location in which it is administered.

5. A tattoo ink according to claim 4, wherein said exogenous energy is selected from the group consisting of thermal energy, light energy, electrical energy, sonic energy, magnetic energy, chemical energy, enzymes, mechanical energy, and combinations thereof.

6. A tattoo ink according to claim 4, wherein the vehicle is a hydrogel.

7. A tattoo ink according to claim 4, wherein the vehicle is a liposome.

8. A tattoo ink according to claim 1, wherein said vehicle comprises a substance that is spontaneously bioabsorbed, biodegraded, or bioeroded to reduce retention of the pigment or dye and permit elimination of the pigment or dye from the location in which it is administered.

9. A tattoo ink according to claim 8, wherein said vehicle is selected from the group consisting of biodegradable polymers.

10. A tattoo ink according to claim 9, wherein the biodegradable polymers are selected from the group consisting of alginates, poly(lactic acid), poly(vinyl alcohol), polyanhydrides, poly(glycolic acid), microporous polyesters, microporous polyethers, cross-linked collagen, and mixtures thereof.

11. A tattoo ink according to claim 1, wherein said pigment or dye comprises particles smaller than 1 micron.

12. A method for producing non-blurring tattoos comprising introducing a tattoo ink according to claim 2 into the dermis of an individual.

13. A method for producing erasable tattoos comprising introducing a tattoo ink according to claim 4 into the dermis of an individual.

14. A method for producing semi-permanent tattoos comprising introducing a tattoo ink according to claim 8 into the dermis of an individual.

15. A tattoo ink according to claim 1, wherein said vehicle is composed of the pigment.

16. A tattoo ink according to claim 4, wherein said vehicle is a microcapsule wherein the shell of the microcapsule is composed of a material which comprises a substance that can be altered by exposure to exogenous energy to release the pigment or dye from the microcapsule.

* * * * *